(12) United States Patent
Kohout

(10) Patent No.: US 6,233,945 B1
(45) Date of Patent: May 22, 2001

(54) EXTENDED LIFE COLD PACK

(75) Inventor: Daniel J. Kohout, Grayslake, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/263,056

(22) Filed: Mar. 6, 1999

(51) Int. Cl.⁷ ..................................................... F25D 5/00
(52) U.S. Cl. ............................................................. 62/4
(58) Field of Search ................................. 62/4; 252/70

(56) References Cited

U.S. PATENT DOCUMENTS

| | | | |
|---|---|---|---|
| 2,573,791 | 11/1951 | Howells | 128/82.1 |
| 3,095,291 | 6/1963 | Robbins | 62/4 |
| 3,149,943 | 9/1964 | Amador | 62/4 |
| 3,175,558 | 3/1965 | Caillouette et al. | 128/403 |
| 3,643,665 | 2/1972 | Caillouette | 128/403 |
| 3,736,769 | 6/1973 | Petersen | 62/530 |
| 3,763,622 | 10/1973 | Stanley, Jr. | 53/25 |
| 3,804,077 | 4/1974 | Williams | 126/263 |
| 3,892,060 | 7/1975 | Stanley, Jr. | 53/127 |
| 3,950,158 | 4/1976 | Gossett | 62/4 |
| 3,957,472 | 5/1976 | Donnelly | 62/4 |
| 3,977,202 | 8/1976 | Forusz et al. | 62/4 |
| 4,049,408 | 9/1977 | Patel | 62/4 |
| 4,081,256 | 3/1978 | Donnelly | 62/4 |
| 4,397,315 | 8/1983 | Patel | 128/403 |
| 4,462,224 | 7/1984 | Dunshee et al. | 62/530 |
| 4,596,250 | 6/1986 | Beisang, III et al. | 128/402 |
| 4,750,493 | 6/1988 | Brader | 128/380 |
| 4,780,117 | 10/1988 | Lahey et al. | 62/4 |
| 4,856,651 | 8/1989 | Francis, Jr. | 206/219 |
| 4,953,550 | 9/1990 | Dunshee | 128/403 |
| 4,967,573 | 11/1990 | Wilhelm | 62/530 |
| 4,993,237 | 2/1991 | Bond et al. | 62/294 |
| 4,995,217 | 2/1991 | Francis, Jr. | 53/410 |
| 5,178,139 | 1/1993 | Angelillo et al. | 128/403 |
| 5,184,613 | 2/1993 | Mintz | 128/402 |
| 5,211,949 | 5/1993 | Salyer | 424/402 |
| 5,261,241 | 11/1993 | Kitahara et al. | 62/4 |
| 5,274,865 | 1/1994 | Takehashi | 5/644 |
| 5,277,180 | 1/1994 | Angelillo et al. | 607/114 |
| 5,314,005 | 5/1994 | Dobry | 165/10 |
| 5,393,462 | 2/1995 | Avery | 252/315.5 |
| 5,409,500 | 4/1995 | Dyrek | 607/111 |
| 5,417,276 | 5/1995 | Dobry | 165/10 |
| 5,417,721 | 5/1995 | Mallasch | 607/108 |
| 5,431,022 | 7/1995 | Abe | 62/4 |
| 5,486,206 | 1/1996 | Avery | 607/104 |
| 5,552,075 | 9/1996 | Salyer | 252/70 |
| 5,603,729 | 2/1997 | Brown et al. | 607/114 |
| 5,650,090 | 7/1997 | Salyer | 252/70 |

Primary Examiner—Corrine McDermott
Assistant Examiner—Malik N. Drake
(74) Attorney, Agent, or Firm—Andrew Rozycki; Donald O. Nickey

(57) ABSTRACT

A cold pack 10 made in accordance with the principles of the present invention includes a container 18. Disposed within the container 18 is a first endotherm-producing chemical 15. Also disposed within the container 18 is a solvent packet 13 and a chemical packet 11. Second endotherm-producing chemical 43 is disposed in the chemical packet 11. First endotherm-producing chemical 15, the solvent packet 13 and the chemical packet 11 are collectively components of the cold pack. Preferably the container 18 is sealed so as to surround and encase the components of the cold pack 10. The first endotherm-producing chemical 15 and the second endotherm-producing chemical 43 are selected to be different. Both the first endotherm-producing chemical 15 and the second endotherm-producing chemical 43 may be selected from among those compounds with a positive enthalpy of solution ($\Delta_{sol}/H°$, kJ/mol) and which produce a reduced temperature of solution that is greater than 10° F. and provide the cold pack 10 with an extended life.

22 Claims, 4 Drawing Sheets

EXTENDED LIFE COLD PACK

FIELD OF THE INVENTION

This invention relates to cold packs whereby reduced temperatures may be generated for extended periods of time. More particularly, this invention relates to cold packs that include but are not limited to a combination of endotherm-producing and solubilizing components in the same cold pack. This invention also relates to means for extending the duration of reduced temperatures of cold packs. Furthermore, this invention relates to a process for making cold packs that provides a duration of reduced temperatures beyond that which may be achieved using conventional cold packs.

BACKGROUND OF THE INVENTION

The use of endotherm-producing chemical systems in cold packs is known. Cold packs are used for the treatment of soreness of muscles, the treatment of injuries such as sprains, to reduce the temperature of food or beverage, and for other related applications. The treatment of injuries and sore muscles using a cold pack is generally referred to as "cold therapy."

In the case of cold therapy, for example, because the swelling associated with the injury or sore muscle begins almost immediately with the onset of the injury, or the stress inducing the soreness, treatment should begin promptly. Accordingly, it is desirable that whatever the source of cold therapy used for such treatment, the cold therapy source should be readily available, easy to use, and capable of providing cold therapy for a duration that is effective in treating the injury or sore muscle.

Cold packs may be of several general types. There are those cold packs that contain an insulating material which, upon cooling in a refrigerator or freezer, gradually warm back to ambient temperature. There are those cold packs that operate via a change of phase of the components of the cold pack. There are also those cold packs that employ chemical components that dissolve endothermically in a solvent.

Examples of cold packs that employ an insulating material are cold packs that contain a gel. Typically, these cold packs are cooled in a refrigerator or freezer. For cold therapy, once cooled, the cold pack is placed on the injured or sore area and thus provide the cold therapy. Typical gels are based on the gelation of xanthan gum, locust bean gum, gum tragacanth, guar gum, hydroxypropyl methylcellulose, absorbent polymers, and the like. Gels may also be based on a high molecular weight polyacrylic acid cross-linked with a polyalkenyl ether, also referred to as a cis-carbomer.

Other examples of cold packs that employ an insulating material exist in the art. For example, cold packs may employ an outer insulative layer. Alternately, clays or silicates may be used to form aqueous colloidal dispersions sometimes referred to as gels. These colloidal dispersions would perform a similar insulating function as do the gels described above.

Phase change materials may be converted between solid and liquid phases and utilize their latent heat of fusion to cool during such phase conversion. The latent heats of fusion are greater than the sensible heat capacities of the materials. Accordingly, the amount of energy absorbed upon melting or released upon freezing is greater than the amount of energy absorbed or released upon increasing or decreasing the temperature of the material by 10° C. Water is one example of a phase change material.

Certain chemical compounds, once dissolved into a solution, result in a lowering of the temperature of the solution below ambient temperature. On dissolution, these compounds take up heat from the surrounding environment. For example, inorganic salts or soluble organic compounds known to have a positive (greater than zero) enthalpy ($\Delta_{sol} H°$) of aqueous solution are used to make the reduced temperature solutions useful in cold packs. However, solvents other than water may be used so long as $\Delta_{sol} H°$ of the solute is greater than zero. Other ingredients may be added as well.

Any of these cold packs may be used in combination. Cold packs which employ a gel may also contain endotherm-producing compounds. Phase change materials may also be used in combination with endotherm-producing compounds.

All of these cold packs require the use of a liquid component. The cold packs described above may contain a liquid or require the addition of a liquid when the cold packs are prepared for use. For example, a gel pack may contain either a gel or a gelation agent. If the cold pack contains the gel, then a liquid, typically water, may already be incorporated into the gel. If the cold pack contains the gelation agent, then a liquid must be added so that the gel may form prior to use of the cold pack. A cold pack that functions based on the use of a phase change material has a liquid phase by definition. A cold pack based on the use of an endotherm-producing chemical is packaged dry and an activating liquid may be added at the time of use. Optionally, such a cold pack may contain an activating liquid kept in a compartment separate from the endotherm-producing chemical until the time of use.

One problem with these conventional cold packs is the short duration of the reduced temperature effect. To be useful in cold therapy, or maintaining food or beverages at a suitable temperature, the cold pack must provide a reduced temperature for a reasonable period of time.

Cold packs of the type that employ endotherm-producing chemicals have employed various methods to extend the cold duration or the "life" of the cold pack. These methods may be divided into three broad categories: (1) physical means to slow dissolution of the endotherm-producing chemical; (2) temperature means to provide a large temperature differential with respect to an ambient temperature; and (3) insulation means to slow the rate of heat absorption in an attempt to increase the time the cold pack is at a reduced temperature.

The first category employs physical means to slow the dissolution of the endotherm-producing chemical. Cold packs of this type have used coated endotherm-producing chemicals whereby the coating slows the dissolution of the chemical. Cold packs of this type have also used endotherm-producing chemicals pressed into pellets. The related prior art teaches that the pellet-form slows the dissolution of the endotherm-producing chemical and thus prolongs the life of the cold pack.

The second category employs a large temperature differential with respect to an ambient temperature. As the temperature differential increases, the time it takes the cold pack to return to an ambient temperature increases. This large temperature differential is accomplished by using two endotherm-producing chemicals whereby one of the chemicals reduces the temperature to an extremely low value and the other chemical reduces the temperature to that useful for cold therapy, for example.

The third category includes those cold packs which also employ gelling agents. These gelling agents may be included in the same container as the endotherm producing chemical. One example of a typical gelling agent is hydroxypropyl methylcellulose. When initiated, the endotherm producing chemical reduces the temperature of the cold pack and the gelling agent gels. The gel thus formed provides some level of insulation to the cold pack.

Each of the above methods for providing a cold pack and extending the cold duration has to some extent proven unreliable or cumbersome. Many conventional cold packs produce a useful reduced temperature of a relatively short duration. Therefore, the cold pack may be ineffective in providing cold therapy or maintaining a food or beverage at a proper reduced temperature. Attempts to extend the reduced temperature duration have presented problems particularly where the cold pack is used to provide cold therapy. If the means to extend the life of the cold pack is based on using a large initial temperature differential, the cold pack will most likely generate a temperature that is too cold for use in cold therapy.

It is generally understood that a cold pack will maintain a reduced temperature for increasing amounts of time as the concentration of endotherm producing chemical increases. It is also generally understood that endotherm producing chemicals are salts, such as ammonium chloride or ammonium nitrate. It is also generally true that cold packs which employ endotherm producing salts are used only one time. Once the cold pack has returned to a temperature at which it is no longer useful as a cold pack, the cold pack must be thrown away. Disposal regulations, however, may limit the amount of the endotherm producing salt which can be used in a cold pack. Therefore, the concentration of endotherm producing salt cannot be increased without limit.

What would therefore be advantageous would be a cold pack having an extended life. It would be advantageous to have a cold pack which avoids the use of potentially costly insulating means. In particular it would be advantageous to have a cold pack which provides an extended life at a useable temperature and which uses a salt concentration which was permissible in view of disposal regulations.

SUMMARY OF THE INVENTION

The present invention provides a cold pack with an extended life. The present invention provides an extended life cold pack that is not based on first establishing an unusable temperature differential with respect to an ambient temperature. The present invention provides an extended life cold pack wherein the extended life is at a conventional temperature of use.

The present invention also provides a method for extending the life of a cold pack that is independent of the particle size of the endotherm-producing chemical. The present invention further provides an improved cold pack that includes but is not limited to an endotherm-producing chemical, means for activating the endotherm-producing chemical, and means for extending the reduced temperature produced by the activated endotherm-producing chemical.

DETAILED DESCRIPTION OF THE INVENTION

Figure 1:
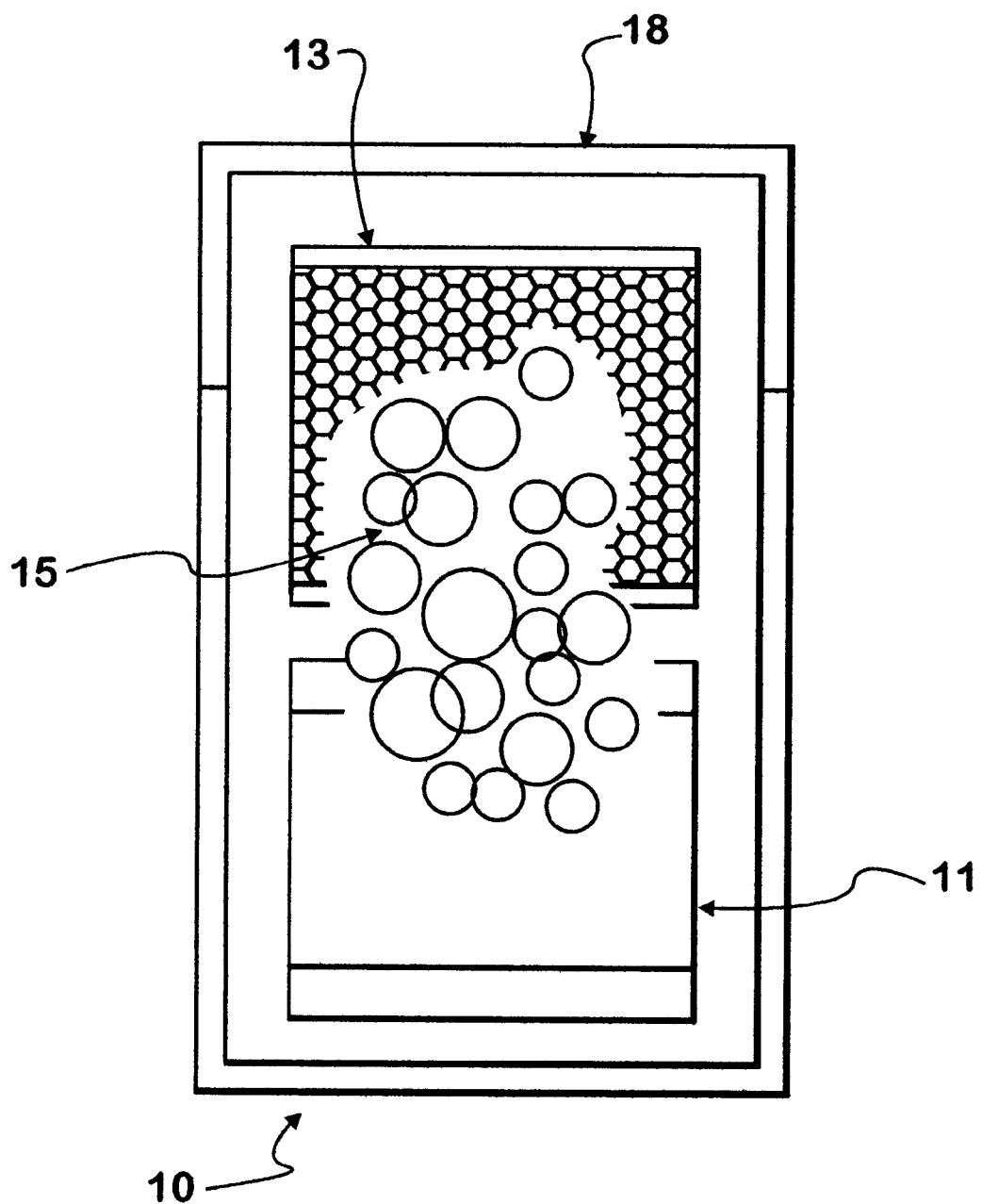
FIG. 1 is a schematic of a cold pack made in a accordance with the principles of the present invention.
Figure 2:
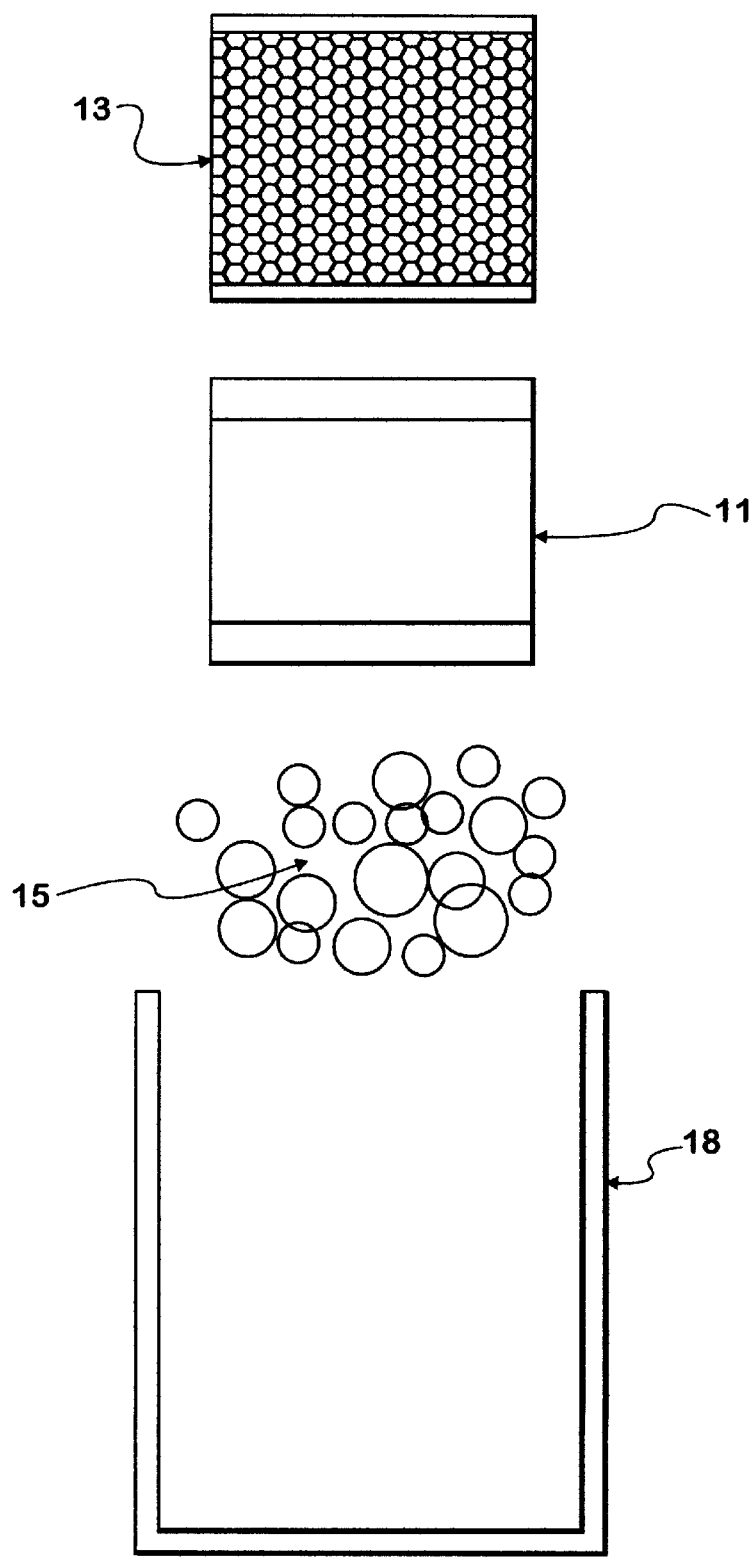
FIG. 2 is an exploded view of the cold pack of FIG. 1.

Referring to FIG. 1, a cold pack made in accordance with the principles of the present invention is designated by 10. The cold pack 10 includes a container 18. Disposed within the container 18 is a first endotherm-producing chemical 15. Also disposed within the container 18 is a solvent packet 13 and a chemical packet 11. The first endotherm-producing chemical 15, the solvent packet 13 and the chemical packet 11 are collectively components of the cold pack. Preferably the container 18 is sealed so as to surround and encase the components of the cold pack. FIG. 2 provides a schematic of the components of the cold pack 10 disassembled from the container 18.

Figure 3:
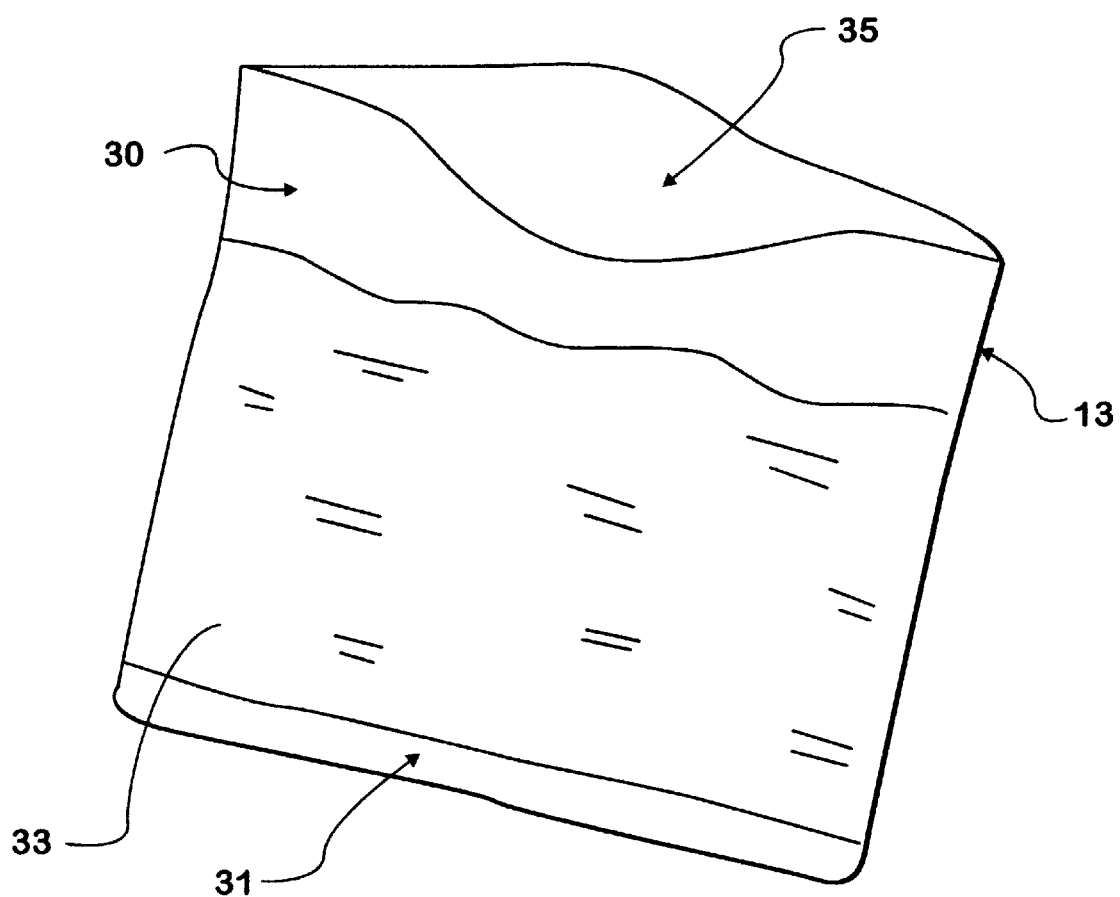
FIG. 3 is a schematic of one of the components of the cold pack of FIG. 1.

Referring to FIG. 3, the solvent packet 13 is illustrated. The solvent packet 13 includes a solvent packet material 30. The solvent packet 13 further includes a bottom seam 31 and an opening 35 thus forming a pouch. Solvent 33 is added to the pouch through the opening 35. In the preferred embodiment, the solvent 33 is water. Thereafter, the opening 35 is sealed so that the solvent packet 13 surrounds and encases the solvent 33. The solvent packet material 30 may be selected from the group of materials which includes polyethylene, polypropylene, polybutylene, polyvinylchloride, polyester, polyethylene terephthalate, vinylidene chloride, and combinations thereof. Combinations of the aforementioned polymers may include laminates, copolymers, and co-extruded films.

Figure 4:
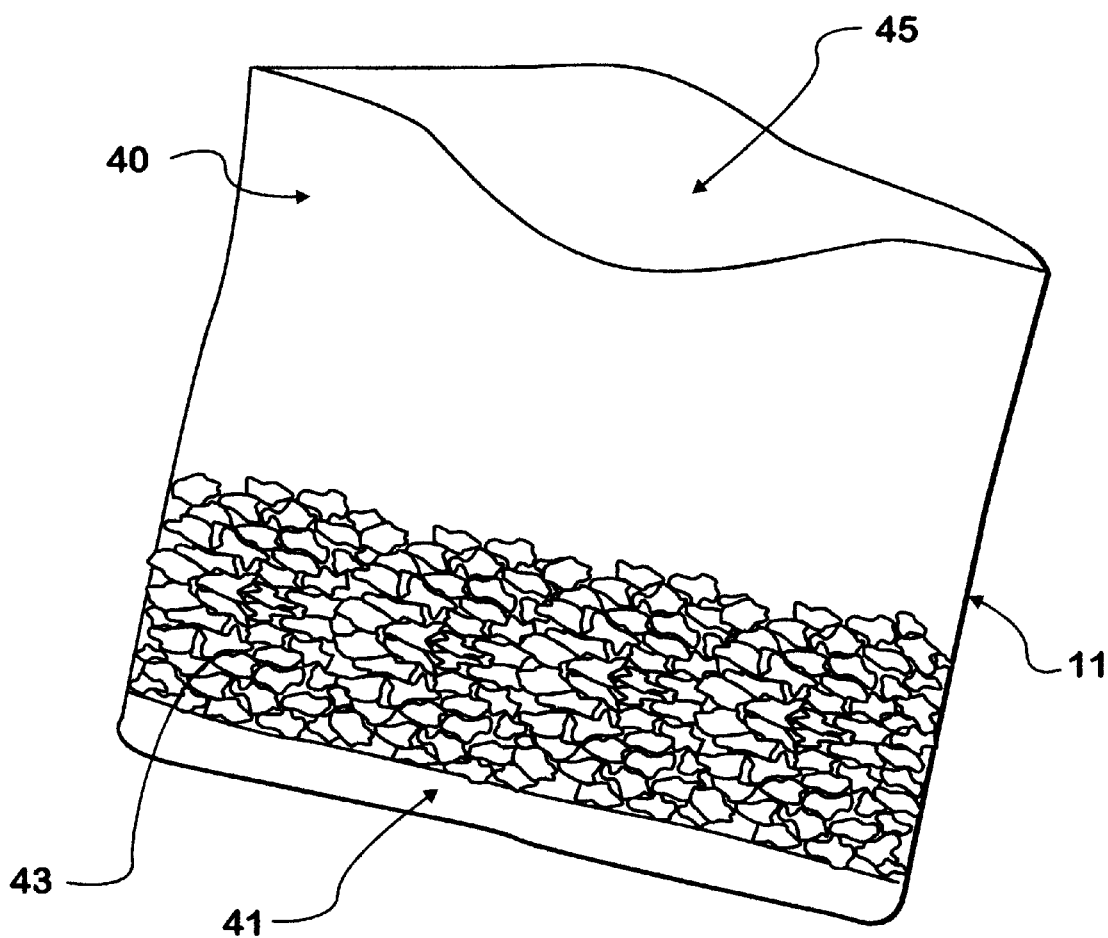
FIG. 4 is a schematic of one of the components of the cold pack of FIG. 1.

Referring to FIG. 4, the chemical packet 11 is illustrated. The chemical packet 11 includes a chemical packet material 40. The chemical packet 11 further includes a bottom seam 41 and an opening 45 thus forming a pouch. A second endotherm-producing chemical 43 is added to the pouch through the opening 45. Thereafter, the opening 45 is sealed so that the chemical packet 11 surrounds and encases the second endotherm-producing chemical 43. The chemical packet material 40 may be selected from the group of materials which includes polyethylene, polypropylene, polybutylene, polyvinylchloride, polyester, polyethylene terephthalate, vinylidene chloride, and combinations of these materials. Combinations of the aforementioned polymers may include laminates, copolymers, and co-extruded films.

Both the solvent packet 13 and the chemical packet 11 are rupturable. Preferably, the solvent packet material 30 of the solvent packet 13 is scored or perforated to facilitate rupturing of the solvent packet material 30. Similarly, it is preferred that the chemical packet material 40 of the chemical packet 11 is scored or perforated so as to facilitate rupturing of the chemical packet 11. Rupturing of the solvent packet material 30 and the chemical packet material 40 allows the solvent 33 and the second endotherm-producing chemical 43, respectively, to contact the first endotherm-producing chemical 15 within the container 18. When the solvent 33, the second endotherm-producing chemical 43 and the first endotherm-producing chemical 15 are in contact with each other the cold pack 10 is said to be activated.

The life of a cold pack 10 is conventionally defined as the time the cold pack 10 remains below 50° F., or 10° C., once it is activated. This is generally without reference to the lowest temperature the cold pack 10 reaches on activation. The temperature may be measured at the surface of the cold pack 10 or within interior of the cold pack 10. A cold pack 10 exhibiting an extended life is one which remains below 50° F. for a longer period of time than a cold pack which uses either the first endotherm-producing chemical 15, or the second endotherm-producing chemical 43, individually such that the total weight of endotherm producing chemicals in both of the cold packs is about the same. It is also desirable that the minimum temperature reached by the cold pack 10, once it is activated at room temperature, be no less than about 10° F., or about 23° C. Room temperature will range from about 65° F. to about 75° F.

The first endotherm-producing chemical 15 may be selected from among those compounds known to react endothermically with the solvent 33. Accordingly, the first endotherm-producing chemical 15 may be selected from the group which includes ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and mixtures of these compounds. More generally, the first endotherm-producing chemical 15 may be selected from among those compounds with a positive enthalpy of solution ($\Delta_{sol}/H°$, kJ/mol) and which produce a reduced temperature of solution that is greater than 10° F. when dissolved in a room temperature solute.

The second endotherm-producing chemical 43 is selected so that the combination of the solvent 33, the first endotherm-producing chemical 15 and the second endotherm-producing chemical 43 results in a cold pack 10 which has an extended life. The second endotherm-producing chemical 43 may be selected from the group which includes ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and mixtures of these compounds, such that the second endotherm producing chemical is different from the first endotherm producing chemical. More generally, the second endotherm-producing chemical 43 may be selected from among those compounds which a positive enthalpy of solution ($\Delta_{sol}/H°$, kJ/mol) and which produce a reduced temperature of solution that is greater than 10° F. when dissolved in a room temperature solute.

Generally, the combination of endothermic reactants is a solute-solute mixture. Such mixtures possess a surprising synergy that produces an extended time at a temperature below 50° F. when compared to the results with either of the solutes separately. Furthermore, this extended life does not rely on a first generation of an extremely cold temperature. Additionally, this extended life does not rely on a change of phase, from a liquid solution to a solid, to generate the extended life of the present invention. This property will be further illustrated in the examples given below.

The first endotherm-producing chemical 15 and the second endotherm-producing chemical 43 are selected to be different. Furthermore, the first endotherm-producing chemical 15 and the second endotherm-producing chemical 43 are selected so that when each is combined with a solvent 33 in a cold pack 10 the effect is to produce an extended life when compared to the use of either of the endotherm-producing chemicals alone. Thus the first endotherm-producing chemical 15 and the second endotherm-producing chemical 43 are selected to provide a synergistic response measured as the extended life of the cold pack 10.

In the preferred embodiment the first endotherm-producing chemical 15 is ammonium nitrate and the second endotherm-producing chemical 43 is urea. However, these compounds may be interchanged with no effect on the performance of the cold pack 10. Thus, in a preferred embodiment, the first endotherm-producing chemical 15 may be urea and the second endotherm-producing chemical 43 may be ammonium nitrate.

To use the cold pack 10 of the present invention, the solvent packet 13 and the chemical packet 11 are ruptured thus allowing the solvent 33, the second endotherm producing chemical 43 and the first endotherm-producing chemical 15 to come into contact with each other. It is preferred that the solvent 33, the second endotherm-producing chemical 43 and the first endotherm-producing chemical 15 are mixed together. This mixing may be accomplished by kneading, rolling, squeezing or shaking the container 18.

A convenient laboratory test has been devised for comparing the effectiveness of different cold pack formulations. In this test, some of the components of the cold pack are placed in a laboratory beaker, or other suitable container, and the temperatures generated therein are measured under mixing. In this test, the life of the cold pack is estimated as the time the beaker contents remain below 50° F., or 10° C., once combined.

EXAMPLE 1

In an example of the efficacy of the solvent, the first endotherm-producing chemical and the second-endotherm producing chemical of the preferred embodiment, ammonium nitrate, urea and water were mixed in a beaker. The temperature of the mixture was measured and the time for the mixture to return to 50° F., measured from the start of the mixing, was recorded. Also, the lowest temperature reached was recorded. Measurements were made on different solutions, in the manner described, wherein the amount of ammonium nitrate and urea were varied. The results of these measurements is presented in table 1 produced below.

TABLE 1

| Time to Reach 50° F. | Lowest Temperature Reached, ° F. | Ammonium Nitrate (grams) | Urea (grams) | Water (grams) |
|---|---|---|---|---|
| 25.4 | 19.2 | 67 | 40 | 100 |
| 31.8 | 16.9 | 67 | 50 | 100 |
| 32.0 | 15.7 | 67 | 60 | 100 |
| 29.8 | 15.5 | 67 | 70 | 100 |
| 41.8 | 13.2 | 67 | 80 | 100 |

As a comparison, ammonium nitrate and water were mixed in a beaker. The temperature of the mixture was measured and the time for the mixture to return to 50° F., or 10° C., measured from the start of the mixing, was recorded. Also, the lowest temperature reached was recorded. Measurements were made on different solutions, in the manner described, wherein the amount of ammonium nitrate was varied. The amounts of ammonium nitrate and water given in table 2 are conventional quantities used in cold packs of the prior art. The results of these measurements are presented in table 2 produced below.

TABLE 2

| Time to Reach 50° F. | Lowest Temperature Reached, ° F. | Ammonium Nitrate (grams) | Urea (grams) | Water (grams) |
|---|---|---|---|---|
| 20.0 | 28.0 | 67 | 0 | 100 |
| 35.0 | 21.7 | 150 | 0 | 100 |
| 26.2 | 26.3 | 100 | 0 | 150 |

TABLE 2-continued

| Time to Reach 50° F. | Lowest Temperature Reached, ° F. | Ammonium Nitrate (grams) | Urea (grams) | Water (grams) |
|---|---|---|---|---|
| 18.3 | 30.4 | 75 | 0 | 112.5 |
| 21.2 | 34.0 | 0 | 67 | 100 |

A comparison of the results of table 1 to the results of table 2 demonstrate that the cold pack of the present invention provides an extended life at a reduced temperature. These results also demonstrate that the cold pack of the present invention does not first establish an unusable lowest temperature. These results further demonstrate that an extended life at a reduced temperature is achieved using conventional amounts of endotherm-producing chemicals.

EXAMPLE 2

Further tests were performed using a circulatory water pad (the "pad"). The pad has an interior pocket into which an extended life cold pack, including endotherm-producing chemicals 15, 43 and solvent 33, may be placed. The interior pocket defines an area for an applied test sample consisting of the cold pack. For these tests, the pad was wrapped two times around a rolled towel. The towel was rolled to simulate a human arm. The temperature of the circulating fluid was set at 99° F. Thermocouple probes were placed on the pad and within the area of an applied test sample. Temperatures of each applied test sample were recorded for a minimum of 40 minutes. Every few minutes during the temperature recording, the applied test sample was slightly agitated, but not removed from the area. This agitation was to simulate a mild level of agitation that occurs in normal use.

In this is example, the performances of the cold packs made according to the present invention were compared to performance of a control cold pack. In the control cold pack, the pad was filled with 218 grams of water and 145 grams of ammonium nitrate. The cold packs of the present invention were prepared by adding different weights of urea to the pad containing 218 grams of water and 145 grams of ammonium nitrate. Table 3, produced below, identifies the compositions tested and the results of this testing. The time shown in table 3 is the elapsed time measured from the activation of the endotherm-producing chemicals. The ambient air temperature in which these tests were conducted was nominally 75° F.

145 grams of ammonium nitrate and 218 grams of water, effectively triples the life of the cold pack as compared to the case where urea is not used. Additionally, an initial temperature of the pack, at 1 minute and at 5 minutes, is effectively unchanged by the incorporation of urea. Thus it can also be seen that the provision of an extended life cold pack according to the principles of the present invention is not simply a matter of increasing the total amount of endotherm-producing chemicals used.

One skilled in the art of cold packs would expect that increasing the amount of endotherm-producing chemicals would result in an increase in the life of the cold pack. Such a relationship is illustrated for the conventional compositions of table 2. Unexpectedly, no such concentration dependency is evident in the present invention, as illustrated by the results of table 1 and table 3. Furthermore, the initial temperature is independent of the amount of second endotherm-producing chemical used.

EXAMPLE 3

In order to further assess the effect of combining a first endotherm-producing chemical and a second endotherm-producing chemical, the heat absorbed by the water in a cold pack was calculated. In this example, a cold pack made according to the principles of the present invention was compared to a conventional cold pack. The heat absorbed is calculated using the following formula:

$$\text{Heat Absorbed (Joules)} = 4.18 \times \Delta T \times W,$$

where $\Delta T$ = the initial temperature—the final temperature (° C.); and $\Delta W$ = the weight of water plus the weight of a calorimeter containing the water.

In performing the experiments for Example 3, water, contained within a sealed pouch, was first placed into a flask and heated to about 155° F. The heated pouch was then placed into a standard laboratory calorimeter equipped with a temperature data log. The calorimeter was positioned on a standard laboratory shaker. The orbital shaker was set to operate at 120 revolutions per minute. The temperature data log was activated and the orbital shaker was activated. The temperature data log and the orbital shaker were in operation throughout the remainder of the experiment. Typically, the temperature in the calorimeter reached an equilibrium value within about 5 minutes of the placement of the heated pouch.

TABLE 3

| Water (grams) | Ammonium Nitrate (grams) | Urea (grams) | Time (minutes) | | | | | | | |
|---|---|---|---|---|---|---|---|---|---|---|
| | | | 1 | 5 | 10 | 15 | 25 | 40 | 60 | 90 | 120 |
| | | | Temperature (° F.) | | | | | | | | |
| 218 | 145 | 0 | 31.1 | 30.0 | 33.8 | 38.3 | 45.4 | 52.2 | 48.7 | | |
| 218 | 145 | 80 | 30.0 | 31.4 | 29.3 | 30.1 | 34.2 | 41.4 | | | |
| 218 | 145 | 145 | 36.5 | 35.2 | 33.7 | 34.2 | 37.1 | 41.4 | 46.7 | 44.0 | 53.9 |

While the results presented in table 1 and table 2 demonstrate the efficacy of the present invention, the results presented in table 3 more closely approximate the results expected from actual use of the cold pack of the present invention. For example, the use of 145 grams of urea, with This equilibration temperature was recorded as the initial temperature. Next, ammonium nitrate and urea were added to the calorimeter, the pouch was ruptured, and the water, urea and ammonium nitrate were allowed to mix. The temperature recorded by the data log was represented as a curve in a plot of temperature as a function of time. Due to the endothermic reaction of the mixture the temperature of the mixture decreased, reached a plateau, and then began to increase. The plateau temperature reached by the mixture was measured by the data log and recorded as the final temperature. The results of Experiment 3 are presented in table 4 below

TABLE 4

| Experiment | 1 | 2 | 3 | 4 |
|---|---|---|---|---|
| Total mixture weight, grams | 555.5 | 538.3 | 539.6 | 530.4 |
| Weight of water, grams | 333.3 | 323.0 | 323.8 | 207.4 |
| Weight of ammonium nitrate, grams | 222.2 | 215.3 | 215.8 | 146.1 |
| Weight of urea, grams | 0 | 0 | 0 | 176.9 |
| Weight of water plus the calorimeter | 926.5 | 993.4 | 865.4 | 1008.6 |
| Initial Temperature, ° F. | 153.0 | 152.5 | 150.8 | 151.0 |
| Final Temperature, ° F. | 135.0 | 136.0 | 132.8 | 129.0 |
| ΔT, ° F. | 18.0 | 16.5 | 18.0 | 22.0 |
| ΔT, ° C. | 10.0 | 9.2 | 10.0 | 12.2 |
| Heat Absorbed, Joules | 38727.70 | 38063.78 | 36173.72 | 51528.25 |
| Heat Absorbed per gram of mixture, Joules | 69.72 | 70.71 | 67.04 | 97.15 |

The results of Example 3 presented in table 4 above illustrate the significantly greater heat absorbing capacity of a cold pack made according to the principles of the present invention. When compared to conventional cold pack compositions, the cold pack of the present invention absorbs at least 24.8% more heat.

There has been provided, in accordance with the present invention, a cold pack possessing an extended life as compared to state-of-the-art cold packs. The present invention provides an extended life cold pack that is not based on first establishing an unusable temperature differential with respect to an ambient temperature. The present invention provides an extended life cold pack wherein the extended life is at a conventional temperature of use. While the invention has been described with specific embodiments, many alternatives, modifications and variations will be apparent to those skilled in the art in light of the foregoing description. Accordingly, it is intended to include all such alternatives, modifications and variations set forth within the spirit and scope of the appended claims.

What is claimed is:

1. A composition for an extended life cold pack comprising:
   a first endotherm-producing chemical;
   a solvent;
   a second endotherm-producing chemical wherein the second endotherm-producing chemical is different from the first endotherm-producing chemical;
   and wherein said first endotherm-producing chemical and second endotherm-producing chemical are selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and combinations thereof;
   such that the combination of the first endotherm-producing chemical, second endotherm-producing chemical, and the solvent produces a temperature in the combination that is equal to or greater than 10° F. and the cold pack is provided with an extended life.

2. The composition of claim 1 wherein the solvent is water.

3. The composition of claim 1 wherein the first endotherm-producing chemical is ammonium nitrate.

4. The composition of claim 1 wherein the second endotherm-producing chemical is urea.

5. The composition of claim 1 wherein the first endotherm-producing chemical exhibits a positive enthalpy of solution ($\Delta_{sol}H°$, kJ/mol) when dissolved in the solvent and wherein the first endotherm-producing chemical produces a reduced temperature of solution that is greater than 10° F.

6. The composition of claim 1 wherein the second endotherm-producing chemical exhibits a positive enthalpy of solution ($\Delta_{sol}H°$, kJ/mol) when dissolved in the solvent and wherein the second endotherm-producing chemical produces a reduced temperature of solution that is greater than 10° F.

7. A cold pack, comprising:
   a container sealed to the atmosphere;
   a first endotherm-producing chemical disposed within the container;
   a rupturable sealable solvent packet disposed within the container;
   the solvent packet further being sealed to the atmosphere;
   a solvent disposed within the solvent packet;
   a rupturable sealable chemical packet disposed within the container;
   the chemical packet further being sealed to the atmosphere;
   a second endotherm-producing chemical disposed within the chemical packet;
   the first endotherm-producing chemical and the second endotherm-producing chemical being different;
   the first endotherm-producing chemical, the second endotherm-producing chemical and the solvent selected such that when the first endotherm-producing chemical, the second endotherm-producing chemical and the solvent are combined the temperature of the combination is equal to or greater than 10° F. and the cold pack is provided with an extended life.

8. The cold pack of claim 7 wherein the solvent is water.

9. The cold pack of claim 7 wherein the first endotherm-producing chemical is selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and combinations thereof.

10. The cold pack of claim 7 wherein the second endotherm-producing chemical is selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and combinations thereof.

11. The cold pack of claim 7 wherein the first endotherm-producing chemical is ammonium nitrate.

12. The cold pack of claim 7 wherein the second endotherm-producing chemical is urea.

13. The cold pack of claim 7 wherein the solvent packet is scored.

14. The cold pack of claim 7 wherein the chemical packet is scored.

15. The cold pack of claim 1 wherein the first endotherm-producing chemical exhibits a positive enthalpy of solution ($\Delta_{sol}H°$, kJ/mol) when dissolved in the solvent and wherein the first endotherm-producing chemical produces a reduced temperature of solution that is greater than 10° F.

16. The cold pack of claim 7 wherein the second endotherm-producing chemical exhibits a positive enthalpy of solution ($\Delta_{sol}$/H°, kJ/mol) when dissolved in the solvent and wherein the second endotherm-producing chemical produces a reduced temperature of solution that is greater than 10° F.

17. A method for extending the life of a cold pack comprising:
   providing a first endotherm-producing chemical;
   providing a solvent;
   providing a second endotherm-producing chemical wherein the second endotherm-producing chemical is different from the first endotherm-producing chemical, and wherein each of the first endotherm-producing chemical, the solvent and the second endotherm-producing chemical are separated;
   combining the first endotherm-producing chemical, the solvent and the second endotherm-producing chemical;
   such that when the first endotherm-producing chemical, the solvent and the second endotherm-producing chemical are combined the temperature of the combination is equal to or greater than 10° F. and the cold pack is provided with an extended life.

18. The method of claim 17 further providing the solvent is water.

19. The method of claim 17 further providing the first endotherm-producing chemical selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and combinations thereof.

20. The method of claim 17 further providing the second endotherm-producing chemical selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, and combinations thereof.

21. The method of claim 17 further providing the first endotherm-producing chemical is ammonium nitrate.

22. The method of claim 17 further providing the second endotherm-producing chemical is urea.

* * * * *